US005665679A

United States Patent [19]

McInnes

[11] Patent Number: 5,665,679
[45] Date of Patent: Sep. 9, 1997

[54] METHOD OF DESICCATING POTATO VINES WITH COPPER ALKYLENEDIAMINE

[75] Inventor: Thomas Bond McInnes, Valdosta, Ga.

[73] Assignee: Griffin Corporation, Valdosta, Ga.

[21] Appl. No.: 544,592

[22] Filed: Oct. 18, 1995

[51] Int. Cl.⁶ .................................................. A01N 59/20
[52] U.S. Cl. ......................................................... 504/164
[58] Field of Search ............................................. 504/164

[56] References Cited

U.S. PATENT DOCUMENTS

| | | | |
|---|---|---|---|
| 2,446,682 | 5/1948 | Whitner | 8/54.2 |
| 2,734,028 | 2/1956 | Domogalla | 210/23 |
| 3,716,351 | 2/1973 | Kunkel et al. | 71/67 |
| 3,900,504 | 8/1975 | Woerner | 260/438.1 |
| 3,930,834 | 1/1976 | Schulteis et al. | 71/67 |
| 4,016,272 | 4/1977 | Akbaev et al. | 424/245 |
| 4,020,180 | 4/1977 | Woerner | 424/294 |
| 4,048,324 | 9/1977 | Kohn | 424/294 |
| 4,361,435 | 11/1982 | Meyers et al. | 71/66 |
| 4,409,358 | 10/1983 | Kraft et al. | 524/527 |
| 4,457,937 | 7/1984 | Sandmeier et al. | 424/272 |
| 4,528,185 | 7/1985 | Kraft et al. | 424/81 |

OTHER PUBLICATIONS

"Plant Pathology—Disease Report," Cooperative Extension Service, Michigan State University and U.S. Department of Agriculture Cooperating, No. 19, Sep. 25, 1972.

"Control of Insects, Diseases and Nematodes on Commercial Vegetables," Cooperative Extension Service, Michigan State University, Extension Bulletin 312, Farm Science Series, 1979.

Binning et al., "Chemical Recommendations for Commercial Potato Production," Cooperative Extension Service, University of Wisconsin, Fact Sheet, Revised Dec., 1972.

Agriculture Canada Research Station, "Potato Late Blight: Controlling New Problems," Agri–Info, Factsheet: 94–1, Jan. 1994.

Johnson, "Experts Give Recommendations for Late Blight Control in 1994," Valley Potato Grower, Jun., 1994.

*Primary Examiner*—S. Mark Clardy
*Attorney, Agent, or Firm*—Jones & Askew

[57] ABSTRACT

There is disclosed a method of desiccating potato vines. The method comprises applying to potato vines an effective amount of an aqueous solution of a copper-alkylenediamine complex, such as a copper-ethylenediamine complex.

18 Claims, No Drawings

METHOD OF DESICCATING POTATO VINES WITH COPPER ALKYLENEDIAMINE

FIELD OF THE INVENTION

The present invention relates generally to the treatment of potato vines, and, more specifically, to the treatment of potato vines in order to kill the vines, to desiccate the vines and to prevent late blight.

BACKGROUND OF THE INVENTION

Copper in various forms has long been applied to green plants as a fungicide. However, the more soluble forms of copper, such as organic copper compounds, e.g., copper sulfate, exhibit phytotoxicity to plants. Attempts to reduce the level of phytotoxicity of copper treatments have resulted in the predominate use of fixed coppers, such as copper hydroxide and copper oxychloride.

Fixed copper compounds are commonly used on potatoes during the growing season for protection against early blight and late blight diseases. At the end of the growth stage of potatoes and maturity of the tubers, the presence of green plant tissue can be a source of inoculum for the late blight disease organism. The organism can then infect the tubers during harvest, leading to increased spoilage during storage. The disease organism can also overwinter on seed tubers causing infection on plants during the subsequent growing season.

To reduce the possibility of late blight infection of tubers, the green tissue of the mature potato vine is killed and desiccated by application of a herbicide prior to harvest. However, only a few herbicides are suitable for this use. One or more fungicides can also be added to the herbicide treatment to kill the blight organisms. Copper sulfate is often used with a herbicide for this purpose since it is a relatively inexpensive form of copper and phytotoxicity is not a concern. If copper sulfate alone is used to treat potato vines, disease control would be adequate but the level of phytotoxicity alone would not be sufficient to reduce the presence of green tissue to an acceptable level.

Therefore, a need exists for a composition which will provide both sufficient desiccation of the potato vine and disease control against late blight with relatively low levels of toxicity to humans and animals.

SUMMARY OF THE INVENTION

The present invention satisfies the above-described needs by providing a method of treating potato vines comprising applying to potato vines an aqueous solution of a water soluble complex of a divalent copper salt and an amine of the formula:

wherein ALK is alkylene of 2 to 3 carbon atoms and each R is independently hydrogen, methyl, or ethyl.

In an alternate embodiment, there is disclosed a method of treating potato vines comprising applying to a potato vines an effective amount of a copper-alkylenediamine complex, such as a copper-ethylenediamine complex. The copper-alkylenediamine complex produces both late blight disease control and satisfactory vine desiccation.

Accordingly, it is an object of the present invention to provide an improved method of treating potato vines.

Another object of the present invention is to provide a treatment which provides both late blight disease control and potato vine desiccation.

A further object of the present invention is to provide a method of treating potato vines which is not detrimental to the tubers associated therewith.

Yet another object of the present invention is to provide a method of treating potato vines with a composition which has relatively low toxicity.

These and other objects, features and advantages of the present invention will become apparent after a review of the following detailed description of the disclosed embodiments and the appended claims.

DETAILED DESCRIPTION OF THE DISCLOSED EMBODIMENTS

The present invention relates to an improved method for treating potato vines. The novel method of the present invention offers both satisfactory potato vine desiccation and late blight disease control. The method comprises applying to potato vines an amount of a copper-mine complex sufficient to desiccate the potato vine. Specifically, the present invention comprises applying to potato vines an aqueous solution of a water soluble complex of a divalent copper salt and an amine of the formula:

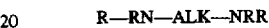

wherein ALK is alkylene of 2 to 3 carbon atoms and each R is independently hydrogen, methyl, or ethyl. The amine to copper mole ratio is from 0.5:1 to 12:1.

Copper-alkylenediamine complexes are well know to those skilled in the art. Copper-alkylenediamines can be produced from water soluble copper salts, such as copper acetate, copper nitrate, copper sulfamate, copper chloride, copper sulfate and the like, or may be produced from water insoluble copper salts, such as basic copper hydroxide, basic copper sulfate, basic copper carbonate, copper oxychloride and the like. The copper containing material is complexed with an alkylenediamine, such as ethylenediamine, propylenediamine, N-methyl ethylenediamine, N,N'-dimethyl-1,3-propanediamine, N-methyl-1,3-propanediamine, N,N,N',N'-tetraethylethylenediamine or poly(aminoalkylene)$_n$-NH$_2$ wherein n is from 2 to 5, such as diethylene triamine, triethylene tetraamine, tetraethylene pentaamine, aminoethyl ethanolamine or mixtures thereof.

The preparation of copper-alkylenediamine complexes is disclosed in U.S. Pat. No. 4,361,435 (the disclosure of which is incorporated by reference). The copper-alkylenediamine complex is prepared by dissolving one or more of the above-referenced copper-containing compounds in an aqueous solution of one or more of the above-referenced alkylenediamines. The aqueous solution contains between approximately 0.10% and 30.0% by weight of the copper-alkylenediamine complex; preferably, approximately 8% by weight of the copper-alkylenediamine complex. Alternately, the copper complex may be isolated as a dry material by crystallization or drying to a solid form, such as by spray drying. This dry material may then be added to water when it is desired to apply the copper-alkylenediamine complex to a potato vine to be treated.

Copper-alkylenediamine complexes are also commercially available. A preferred copper-alkylenediamine complex is available under the name KOMEEN® from Griffin Corporation, Valdosta, Ga. KOMEEN® is an aqueous solution of a copper-ethylenediamine complex which contains 8% by weight copper metal equivalent. Heretofore, KOMEEN® was known only as an aquatic herbicide.

The copper-alkylenediamine complex can be applied to potato vines by any conventional method, such as by spraying (either aerial or ground) or by chemigation at a rate of between approximately 1 and 10 lbs. copper metal equivalent per acre; preferably, approximately 4.8 lbs. copper metal equivalent per acre. Aqueous solution of the copper-alkylenediamine complex can be applied to potato vines at a rate of between approximately 3 and 20 gallons of aqueous solution per acre.

The copper-alkylenediamine complex of the present invention may be applied to potato vines at tuber maturity prior to harvest.

Optionally, the aqueous solution of the copper-alkylenediamine complex can contain adjuvants that enhance the wetting and penetration of plant tissue. Adjuvants which are useful in the present invention include wetting agents, such as anionic and nonionic surfactants, adhesion promoting agents including resins and polymers, organosilicone and fluorine containing surfactants and the like. These agents may be added to the copper-alkylenediamine complex at a rate of between approximately 0.5% and 15% by weight or may be added separately to the diluted spray mixture prior to application to the potato vines.

The following examples are illustrative of the present invention and are not intended to limit the scope of the invention as set forth in the appended claims. All temperatures are in degrees Celsius and all percentages are by weight unless specifically stated otherwise.

EXAMPLE 1

A comparative test was performed on Irish potatoes, Cultivar ND 860 early season round white. The test plot was four 38" rows×70' non-replicated strip plots. Maintenance pesticides were applied to the plot twice during the growing season. Fourteen weeks after planting, the potato vines were treated with various test solutions which are described below. The method of application was by ground sprayer delivering 20 gal. per acre at a pressure of 40 psi. Various test treatments were prepared as shown in Table 1.

TABLE 1

| Treatment | Composition |
| --- | --- |
| 1 | Diquat 1 pt./acre + X-77 (0.25% v/v) |
| 2 | Diquat 1 pt./acre + X-77 (0.25% v/v) + copper sulfate pentahydrate 10 lbs./acre |
| 3 | Diquat 1 pt./acre + X-77 (0.25% v/v) + Komeen 3 gal./acre |
| 4 | Diquat 1 pt./acre + Kocide LF 5 1/3 pt./acre + LI 700 2 pt./100 gal. (acidified to pH 4–4.5) |
| 5 | Diquat 1 pt./acre + Kocide 101 4 lbs./acre + LI 700 2 pt./100 gal. (acidified to pH 4–4.5) |
| 6 | Komeen 6 gal./acre + Kinetic 8 fl. oz./acre |
| 7 | Copper sulfate pentahydrate 10 lbs./acre + LI 700 2 qt./acre |
| 8 | Untreated control |

Diquat ® is 1, 1' ethylene-2,2' dipyridinium dibromide. X-77 is a surfactant consisting of alkylaryloxyethylene, free fatty acids and glycols (available from Loveland Industries). Komeen is an 8% by weight copper metal equivalent aqueous solution of copper-ethylenediamine complex (0.8 lbs. of mettallic copper per gal.) (available from Griffin Corporation, Valdosta, Georgia). Kocide LF is a 15% by weight copper metal equivalent aqueous suspension of copper hydroxide (2.4 lbs. copper hydroxide per gal.) (available from Griffin Corporation, Valdosta, Georgia). LI 700 is a surfactant derived from an organic acid and a processed soybean derivative (available from Loveland Industries). Kocide 101 is 50% by weight copper metal equivalent copper hydroxide wettable powder (available from Griffin Corporation, Valdosta, Georgia). Kinetic is an organosilicone surfactant (available from Setre Chemical).

The treated potato vines were observed at 1 day, 3 day and 7 day intervals and the observations regarding vine desiccation were recorded. The recorded observations for the various treatments are shown below in Table 2.

TABLE 2

| | Foliar Desiccation Ratings | | |
| --- | --- | --- | --- |
| Treatment No. | Day 1 | Day 3 | Day 7 |
| 1 | 4 | 5.5 | 7.5 |
| 2 | 3 | 4.5 | 7.0 |
| 3 | 5.5 | 7.5 | 9.0 |
| 4 | 3.5 | 4.0 | 5.5 |
| 5 | 3.5 | 4.5 | 5.5 |
| 6 | 5.5 | 7.0 | 9.0 |
| 7 | 2.5 | 3.5 | 4.5 |
| 8 | 1 | 1 | 2.5 |

The foregoing ratings are based upon a potato foliar desiccation rating system shown in Table 3 below.

TABLE 3

| Rating | Description |
| --- | --- |
| 1 | Plants healthy - no discoloration |
| 2 | Slight leaf discoloration |
| 3 | 5% leaf discoloration |
| 4 | 25% leaf discoloration |
| 5 | 50% leaf discoloration |
| 6 | 75% leaf discoloration |
| 7 | 90% leaf discoloration - stem 10% dead |
| 8 | All leaves gone - stem 10% dead |
| 9 | All leaves gone - stem 90% dead |
| 10 | Plants completely dead |

From the foregoing test results, it can be seen that the treatment using only the copper-ethylenediamine complex (Treatment No. 6) was as effective, or in some cases more effective, at potato vine desiccation than were the treatments using the herbicide Diquat (Treatment Nos. 1–5). In contrast, those vines treated only with copper sulfate pentahydrate (Treatment No. 7) did not achieve satisfactory vine desiccation by the end of the test.

EXAMPLE 2

The same procedure as described in Example 1 above is followed except that different copper-alkylenediamine complexes are tested. The various complexes are reported in Table 4 shown below:

TABLE 4

| Formula No.. | Copper-Alkylenediamine Complex |
| --- | --- |
| 1 | copper-propylenediamine complex |
| 2 | copper-N-methyl ethylenediamine complex |
| 3 | copper-N,N' -dimethyl-1,3-propanediamine complex |
| 4 | copper-N-methyl-1,3-propanediamine complex |
| 5 | copper-N,N,N',N'-tetraethylethylenediamine complex |
| 6 | copper-diethylene triamine complex |
| 7 | copper-triethylene tetraamine complex |
| 8 | copper-tetraethylene pentaamine complex |
| 9 | copper-aminoethyl ethanolamine complex |

All of the foregoing formulations produce satisfactory potato vine desiccation.

EXAMPLE 3

The same procedure as described in Example 1 above is followed except that different amounts of copper-ethylenediamine complexes are tested. The various amounts are reported in Table 5 shown below:

TABLE 5

| Formula No.. | Copper-Ethylenediamine Complex (Komeen) |
|---|---|
| 1 | 3 gal./acre |
| 2 | 5 gal./acre |
| 3 | 10 gal./acre |
| 4 | 20 gal./acre |

All of the foregoing formulations produce satisfactory potato vine desiccation.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of desiccating potato vines comprising applying to said potato vines an effective amount of an aqueous solution of a copper-alkylenediamine complex such that said potato vines are desiccated thereby.

2. The method of claim 1, wherein said copper-alkylenediamine complex is in the form of an aqueous solution.

3. The method of claim 2, wherein said aqueous solution is applied to said potato vines by spraying.

4. The method of claim 1, wherein said copper-alkylenediamine complex is applied to said potato vines at a rate of between approximately 0.1 and 7 lbs. copper metal equivalent per acre.

5. The method of claim 1, wherein said copper-alkylenediamine complex is applied to said potato vines at a rate of approximately 4.8 lbs. copper metal equivalent per acre.

6. The method of claim 2, wherein said aqueous solution contains between approximately 0.10% and 30.0% by weight copper metal equivalent.

7. The method of claim 2, wherein said aqueous solution contains approximately 8% by weight copper metal equivalent.

8. The method of claim 6, wherein said aqueous solution is applied to said potato vines at a rate of between approximately 3 and 20 gallons per acre.

9. The method of claim 7, wherein said aqueous solution is applied to said potato vines at a rate of approximately 6 gallons per acre.

10. A method of preventing late blight disease and desiccating potato vines comprising applying to a potato vine an amount of a copper-ethylenediamine complex sufficient to both prevent late blight disease and to desiccate said potato vines.

11. A method of killing a potato vine comprising applying to said potato vine an amount of an aqueous solution of a copper-ethylenediamine complex sufficient to kill said potato vine.

12. A method of desiccating potato vines comprising applying to said potato vines an effective amount of an aqueous solution of a water soluble complex of a divalent copper salt and an amine of the formula:

R—RN—ALK—NRR wherein ALK is alkylene of 2 to 3 carbon atoms and each R is independently hydrogen, methyl, or ethyl, such that said potato vines are desiccated thereby.

13. The method of claim 12, wherein said copper salt is selected from the group of copper acetate, copper nitrate, copper sulfamate, copper chloride, copper sulfate and mixtures thereof.

14. The method of claim 12, wherein said copper salt is selected from the group of copper hydroxide, basic copper sulfate, basic copper chloride, basic copper carbonate, copper oxychloride and mixtures thereof.

15. The method of claim 12, wherein said amine is selected from the group of ethylenediamine, propylenediamine, N-methyl ethylenediamine, N,N'-dimethyl-1,3-propanediamine, N-methyl-1,3-propanediamine, N,N,N',N'-tetraethylethylenediamine and mixtures thereof.

16. The method of claim 2, wherein said amine is poly (aminoalkylene)$_n$-NH$_2$ wherein n is from 2 to 5.

17. The method of claim 12, wherein said amine is selected from the group of diethylene triamine, triethylene tetraamine, tetraethylene pentaamine, aminoethyl ethanolamine and mixtures thereof.

18. The method of claim 12, wherein said amine is ethylenediamine.

* * * * *